(12) United States Patent
Sanford et al.

(10) Patent No.: US 6,916,324 B2
(45) Date of Patent: Jul. 12, 2005

(54) PROVISIONAL ORTHOPEDIC PROSTHESIS FOR PARTIALLY RESECTED BONE

(75) Inventors: Adam H. Sanford, Warsaw, IN (US); Scott C. Lazar, Cromwell, IN (US); Scott J. Steffensmeier, Warsaw, IN (US); Richard V. Williamson, Ana Cortes, WA (US)

(73) Assignee: Zimmer Technology, Inc., Chicago, IL (US)

( * ) Notice: Subject to any disclaimer, the term of this patent is extended or adjusted under 35 U.S.C. 154(b) by 211 days.

(21) Appl. No.: 10/357,610

(22) Filed: Feb. 4, 2003

(65) Prior Publication Data

US 2004/0153162 A1 Aug. 5, 2004

(51) Int. Cl.$^7$ .................................................. A61F 5/00
(52) U.S. Cl. ........................................ 606/87; 606/88
(58) Field of Search ............................ 606/80, 86, 87, 606/88, 89; 623/20.35

(56) References Cited

U.S. PATENT DOCUMENTS

| | | | | |
|---|---|---|---|---|
| 4,825,857 A | * | 5/1989 | Kenna | 606/88 |
| 5,258,032 A | * | 11/1993 | Bertin | 623/20.35 |
| 5,423,827 A | * | 6/1995 | Mumme et al. | 606/96 |
| 5,445,642 A | | 8/1995 | McNulty et al. | |
| 5,458,645 A | * | 10/1995 | Bertin | 128/898 |
| 5,464,406 A | * | 11/1995 | Ritter et al. | 606/86 |
| 5,514,139 A | | 5/1996 | Goldstein et al. | |
| 5,520,695 A | | 5/1996 | Luckman | |
| 5,597,379 A | | 1/1997 | Haines et al. | |
| 5,643,272 A | | 7/1997 | Haines et al. | |
| 5,662,656 A | * | 9/1997 | White | 606/88 |
| 5,702,460 A | * | 12/1997 | Carls et al. | 606/79 |
| 5,720,752 A | * | 2/1998 | Elliott et al. | 606/88 |
| 5,755,803 A | | 5/1998 | Haines et al. | |
| 5,776,201 A | * | 7/1998 | Colleran et al. | 623/20.15 |
| 5,810,827 A | | 9/1998 | Haines et al. | |
| 5,860,980 A | * | 1/1999 | Axelson et al. | 606/88 |
| 5,879,354 A | | 3/1999 | Haines et al. | |
| 5,925,049 A | * | 7/1999 | Gustilo et al. | 606/82 |
| 5,989,261 A | | 11/1999 | Walker et al. | |
| 6,056,754 A | | 5/2000 | Haines et al. | |
| 6,080,196 A | | 6/2000 | Bertin | |
| 6,096,043 A | | 8/2000 | Techiera et al. | |
| 6,159,217 A | * | 12/2000 | Robie et al. | 606/88 |
| 6,197,064 B1 | | 3/2001 | Haines et al. | |
| 6,413,261 B1 | * | 7/2002 | Grundei | 606/87 |
| 6,488,687 B1 | * | 12/2002 | Masini | 606/88 |
| 6,500,179 B1 | * | 12/2002 | Masini | 606/88 |
| 6,575,980 B1 | * | 6/2003 | Robie et al. | 606/88 |
| 6,695,848 B2 | | 2/2004 | Haines et al. | |
| 2003/0225413 A1 | * | 12/2003 | Sanford et al. | 606/87 |

OTHER PUBLICATIONS

Informational Pamphlet—Zimmer 1999, *Revision Knee Arthroplasty Surgical Guidelines*, pp. 1–39.

(Continued)

*Primary Examiner*—Corrine McDermott
*Assistant Examiner*—Thomas J Sweet
(74) *Attorney, Agent, or Firm*—Jonathan Feuchtwang; Baker & Daniels

(57) ABSTRACT

A provisional orthopedic prosthesis having a first provisional component and an optional second component. The provisional prosthesis may be a partial knee prosthesis and is used to assess the fit of a permanent prosthesis having first and second components. The first provisional component has a size which differs from the first permanent component and is mountable on a bone which has been only partially prepared to receive the first permanent component. Providing a provisional component which is mounted on a partially prepared bone, simplifies the preparation of the bone for a differently sized component if the provisional indicates that the preliminarily selected permanent component is incorrectly sized.

23 Claims, 3 Drawing Sheets

OTHER PUBLICATIONS

Brochure—Zimmer 2002, MIS Minimally Invasive Solution, Intramedullary Surgical Approach, *The M/G Unicompartmental Knee Minimally Invasive Surgical Technique*, pp. 1–24.

Brochure—Zimmer 1998, 2000—NexGen Complete Knee Solution, *Multi–Reference 4–in–1 Femoral Instrumentation Posterior Reference Surgical Technique*, pp. 1–16.

Brochure—Zimmer 1995, 1997, 1998—NexGen Complete Knee Solution, *Intramedullary Instrumentation Surgical Technique*, pp. 1–33.

Brochure—Zimmer 2001—NexGen Complete Knee Solution, *Revision Instrumentation Surgical Technique for Legacy Knee Constrained Condylar Knee*, pp. 1–78.

* cited by examiner

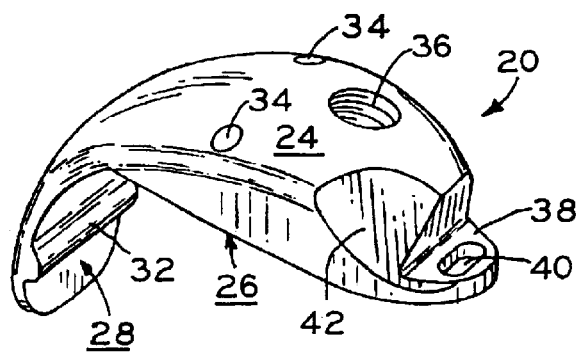
FIG_1
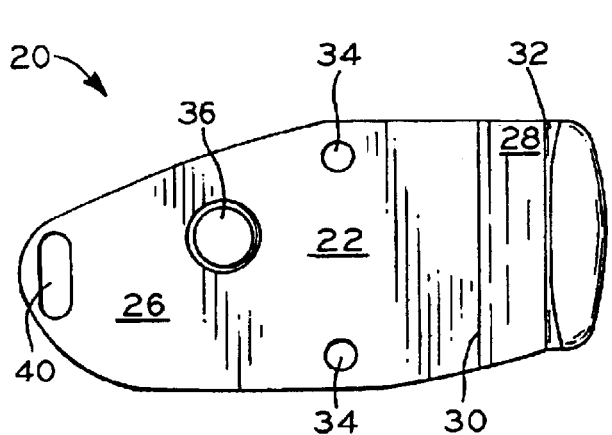
FIG_2
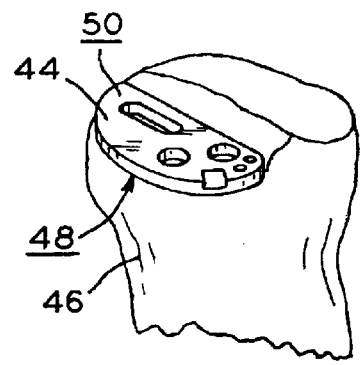
FIG_8
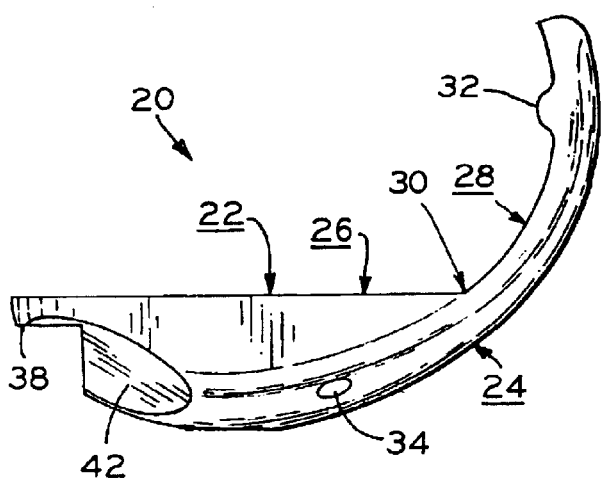
FIG_3
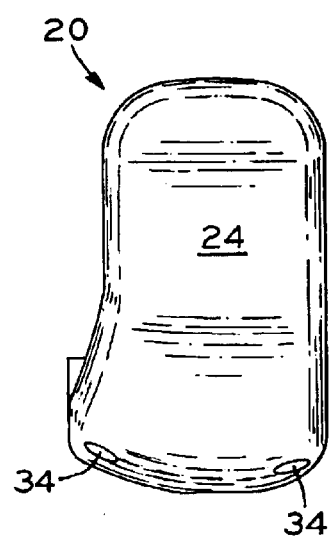
FIG_4

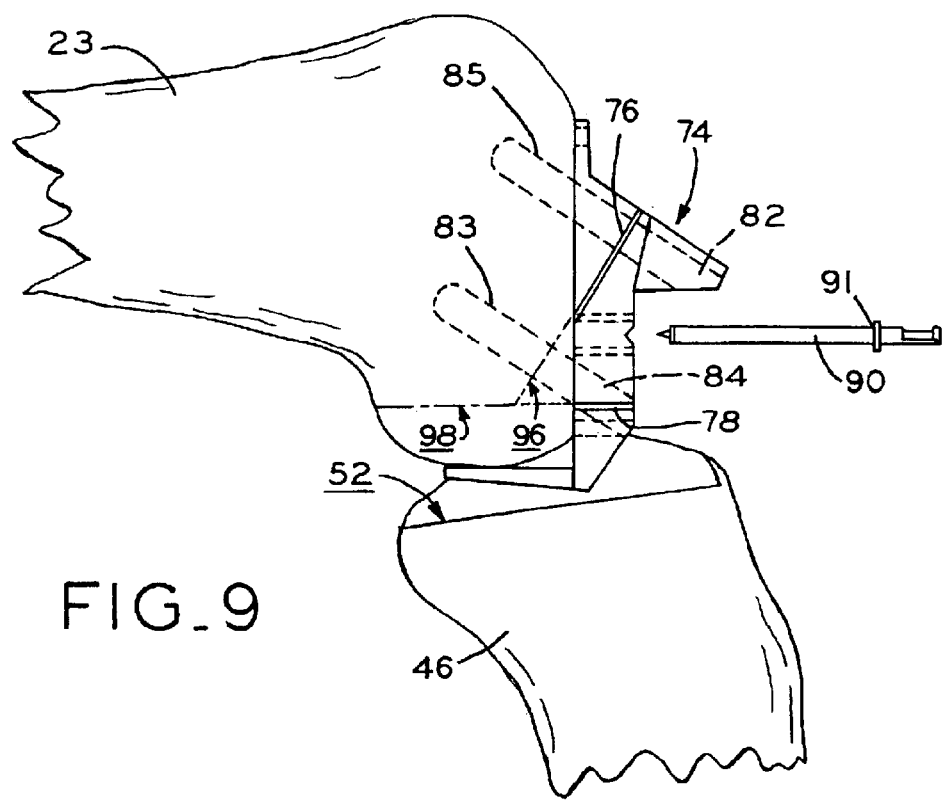
FIG._9
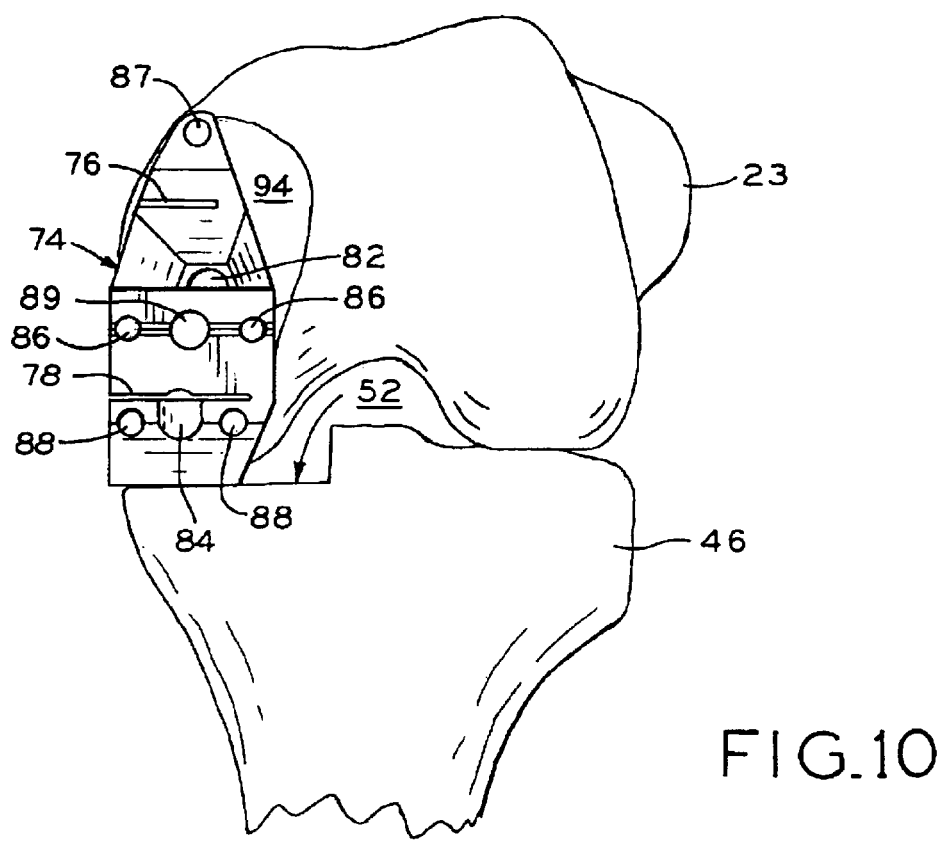
FIG.10

US 6,916,324 B2

PROVISIONAL ORTHOPEDIC PROSTHESIS FOR PARTIALLY RESECTED BONE

BACKGROUND OF THE INVENTION

1. Field of the Invention

The present invention relates to orthopedic prostheses and, more specifically, to provisional components used during orthopedic surgery to facilitate the selection of a permanent orthopedic prosthesis.

2. Description of the Related Art

The use of orthopedic implants to form artificial joints such as prosthetic knees is well known in the art. During a conventional surgical procedure to implant a prosthetic knee joint, a provisional femoral component and a provisional tibial component are placed on the distal femur and proximal tibia after resecting the distal femur and proximal tibia to confirm the proper size and position of the permanent femoral and tibial components. The provisional components typically come in a range of sizes which are identical in size and shape to the permanent components. The provisional components which are placed on the resected femur and tibia are typically selected after making a preliminary determination of the proper size. A trial reduction of the knee joint with the provisional components in place may indicate that the preliminary size determination was incorrect, that the gap between the femur and tibia is insufficient, or some other undesirable characteristic which requires the selection of a different sized tibial or femoral component thereby necessitating the further resection of either the tibia or femur.

Resection of the femur generally involves making three or four intersecting generally planar cuts and making changes to one such cut may require changes in the remaining cuts. The tibial plateau, on the other hand, generally only involves a single cut and provides a more convenient location for corrective actions. It is generally desirable to leave as much healthy bone stock as possible when implanting either total or partial prosthetic knee joints. It is particularly desirable to leave as much healthy bone stock as possible when implanting a unicompartmental or partial knee prosthesis which involves the removal of only a single condyle. This is due to the possibility that the remaining natural condyle may require replacement at a later date and leaving a greater amount of bone stock facilitates the later removal of the partial prosthetic joint and the implantation of a total prosthetic knee joint. Consequently, an improved system which facilitates the proper sizing, selection and positioning of the prosthetic components while minimizing the risk of having to conduct additional bone resections after a trial reduction of the initial provisional components would be desirable.

SUMMARY OF THE INVENTION

The present invention provides an improved provisional orthopedic prosthesis that may be placed on a partially resected bone to facilitate the proper selection or positioning of the permanent prosthesis and thereby minimize the risk of having to make corrective cuts on the partially resected bone. Such a provisional prosthesis may be used when implanting a prosthetic knee joint and may take the form of a provisional uni-condylar femoral component.

By providing a provisional component which can be mounted on a partially resected bone, the fit of the preliminarily selected permanent prosthetic component can be assessed prior to fully preparing the bone to receive the permanent component. In the event that the provisional component indicates that a differently sized permanent component should be selected, it will generally be advantageous that the bone was not fully prepared to receive the originally selected size.

The invention comprises, in one form thereof, a provisional orthopedic prosthesis for facilitating the selection of a permanent orthopedic prosthesis. The permanent orthopedic prosthesis has a permanent component with a bone engaging surface, an oppositely disposed articulating surface and defines a permanent component spacing therebetween. The provisional prosthesis includes a first provisional component having an inwardly facing surface and an outwardly facing surface. The inwardly facing surface has a first portion defining a configuration substantially similar to a portion of the bone engaging surface of the permanent component and a second portion adapted for placement facing a non-resected bone surface. The outwardly facing surface defines a first articulating surface which is at least partially disposed opposite each of the first and second portions of the inwardly facing surface. A provisional spacing is defined between the outwardly facing surface and the first portion of the first provisional component which is greater than the permanent component spacing. In some embodiments, the provisional spacing is approximately six to eight millimeters greater than the permanent component spacing.

The first provisional component may also include at least one guide element having a predefined position relative to said first portion. The at least one guide element may take the form of an opening extending from the outwardly facing surface to the first portion of the inwardly facing surface. The inwardly facing surface of the first provisional component defines a volume which is greater than the volume defined by the bone engaging surface of the permanent prosthesis.

The provisional orthopedic prosthesis may also include a second provisional component mountable on a second bone and having a second bearing surface engageable with said first articulating surface and a mounting surface engagable with a resected bone surface. The first and second provisional components define a provisional mounting distance between the first portion of the inwardly facing surface and the mounting surface wherein the provisional mounting distance is substantially equivalent to a corresponding mounting distance occupied by the permanent orthopedic prosthesis. The first provisional component of such a prosthesis may be adapted for placement on a distal femur wherein the articulating surface of the first provisional component defines a single condylar-shaped projection and wherein the second provisional component is adapted for placement on a proximal tibia.

The invention comprises, in another form thereof, a provisional orthopedic prosthesis for facilitating the selection of a permanent orthopedic prosthesis. The permanent orthopedic prosthesis has a permanent component with a bone engaging surface defining a plurality of intersecting planar surfaces, an oppositely disposed articulating surface and defines a permanent component spacing therebetween. The provisional prosthesis includes a first provisional component having an inwardly facing surface and an outwardly facing surface. The inwardly facing surface has a first portion defining a substantially planar surface lying within a single plane and configured substantially similar to a portion of the bone engaging surface of the corresponding permanent prosthesis and a second portion positionable proximate a non-resected bone surface. The inwardly facing surface defines a volume greater than the volume defined by the bone engaging surface of the permanent prosthesis. The outwardly facing surface of the first provisional component defines a first articulating surface at least partially disposed opposite each of the first and second portions of the inwardly facing surface. The provisional component also defines a provisional spacing between the outwardly facing surface and the first portion that is greater than the permanent component spacing.

The invention comprises, in yet another form thereof, an orthopedic prosthesis system which includes a permanent prosthesis and a first provisional component. The permanent prosthesis includes a first permanent component defining a bone engaging surface and an oppositely disposed articulating surface. The bone engaging surface and the articulating surface define a permanent component spacing therebetween. The first provisional component has an inwardly facing surface and an outwardly facing surface. The inwardly facing surface has a first portion defining a configuration substantially similar to a portion of the bone engaging surface and a second portion adapted for placement facing a non-resected bone surface. The outwardly facing surface of the first provisional component defines a first articulating surface at least partially disposed opposite each of the first and second portions of the inwardly facing surface. The first provisional component defines a provisional component spacing between the outwardly facing surface and the first portion wherein the provisional component spacing is greater than the permanent component spacing. The provisional component defines a second thickness between the second portion of the inwardly facing surface and the outwardly facing surface wherein a substantial portion of the second thickness is less than the difference between the provisional component spacing and the permanent component spacing.

The system may also include an alignment member removably securable to the bone wherein the first provisional component includes at least one guide element for positioning the alignment member relative to the bone and wherein the system also includes an instrument guide alignable with the alignment member.

The invention comprises, in another form thereof, a method of implanting an orthopedic prosthesis at a joint between a first bone and a second bone. The method includes providing a provisional prosthesis and a corresponding permanent prosthesis. The permanent prosthesis has first and second permanent components. The first permanent component has a bone engaging surface and an oppositely disposed articulating surface defining a permanent component spacing therebetween. The provisional prosthesis has a first provisional component having an inwardly facing surface and an outwardly facing surface. The inwardly facing surface has a first portion defining a configuration substantially similar to a portion of the bone engaging surface and a second portion adapted for placement facing a non-resected bone surface. The method includes partially preparing the first bone to receive the permanent component and mounting the first provisional component on the first bone wherein the outwardly facing surface of the first provisional component opposite the first portion of the inwardly facing surface is spaced outwardly from the bone by a distance which is greater than the permanent component spacing. The method also includes assessing the fit of the provisional prosthesis and completing the preparation of the first bone after assessing the fit of the provisional prosthesis.

The step of partially preparing the first bone may include resecting a portion of the first bone to form a substantially planar resection surface, the step of mounting the first provisional component to the first bone may include engaging a first portion of the inwardly facing surface with the resection surface and positioning a second portion of the inwardly facing surface adjacent a non-resected surface of the first bone, and the step of completing the preparation of the first bone may include resecting a portion of the first bone defined by the non-resected surface of the first bone.

The method may also include the step of at least partially preparing the second bone to receive the permanent prosthesis and wherein the steps of partially preparing the first and second bones defines a gap between first and second prepared surfaces located respectively on the first and second bones and the step of assessing the fit of the provisional prosthesis includes assessing the fit of the provisional prosthesis within the gap.

The method may also include providing a provisional prosthesis that includes a second provisional component mountable on the second bone and having a second bearing surface engageable with the outwardly facing surface of the first provisional component and a mounting surface engageable with the second bone. Such first and second provisional components may define a provisional mounting distance between the first portion of the inwardly facing surface of the first provisional component and the mounting surface of the second provisional component wherein the provisional mounting distance is substantially equivalent to a corresponding mounting distance occupied by the permanent prosthesis. The step of assessing the fit of the provisional prosthesis within the gap may include positioning the first and second provisional components to separate the first and second bones by the provisional mounting distance.

An advantage of the present invention is that it provides a provisional component which can be mounted on a partially resected bone to assess the fit of a permanent component. In the event that the preliminarily selected permanent component is determined to be the incorrect size, the bone will not have been fully prepared to accept an incorrectly sized component and preparing the bone to accept a different component will be greatly simplified. This may also reduce the quantity of healthy bone stock which must be removed in the event of such a change in component sizes.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 1 is a perspective view of a provisional femoral component in accordance with the present invention.

FIG. 2 is a top view of the provisional component of FIG. 1.

FIG. 3 is a side view of the provisional component of FIG. 1.

FIG. 4 is a posterior view of the provisional component of FIG. 1.

FIG. 8 is a perspective view of a provisional component mounted on a tibia.

FIG. 9 is a side view of an instrument guide mounted on a femur.

FIG. 10 is a view of the instrument guide of FIG. 9.

Figure 5:
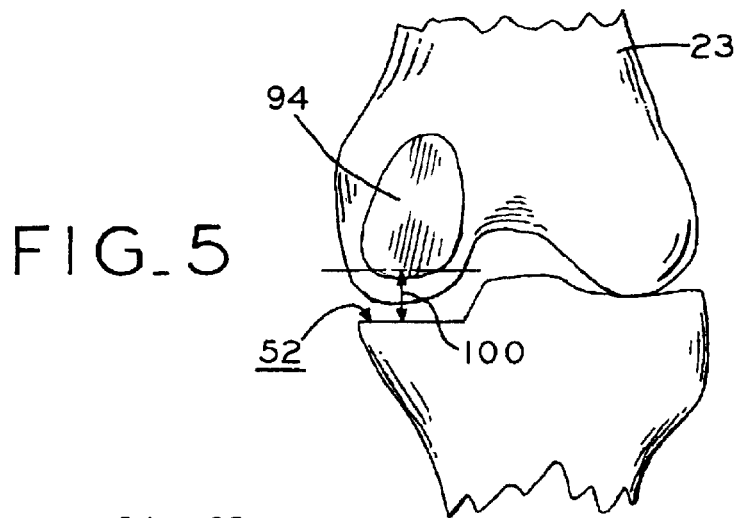
FIG. 5 is a view of a resected tibia and a partially resected femur.

Corresponding reference characters indicate corresponding parts throughout the several views. Although the exemplification set out herein illustrates an embodiment of the invention, the embodiment disclosed below is not intended to be exhaustive or to be construed as limiting the scope of the invention to the precise form disclosed.

DESCRIPTION OF THE PRESENT INVENTION

A provisional orthopedic component 20 in accordance with the present invention is shown in FIGS. 1–4. In the illustrated embodiment, component 20 is a provisional femoral component which is removably mountable on the distal end of a femur 23 and is used in a surgical procedure implanting a unicompartmental prosthetic knee joint. Provisional component 20 has a first inwardly facing surface 22 and an oppositely disposed second outwardly facing surface 24. In the illustrated embodiment, inwardly facing surface 22 includes a first portion 26 which is substantially planar and a second portion 28. First and second surface portions 26, 28 intersect at line 30. A small projection 32 is located on second portion 28 of inwardly facing surface 22 and is positioned to engage an outer surface of a posterior femur when provisional component 20 is mounted on the femur. Openings 34 extend between outwardly facing surface 24 and inwardly facing surface 22 and take the form of cylindrical passages in the illustrated embodiment. Openings 34 form guide elements as discussed in greater detail below.

A threaded opening 36 is also located on provisional component 20. A T-shaped device (not shown) having a threaded end may be engaged with opening 36 to manipulate provisional component 20 during a surgical procedure. A relatively thin plate-like projection 38 extends from the anterior end of provisional component 20 and defines an oval opening 40. A securement member such as a bone screw may be inserted through opening 40 to temporarily secure provisional component 20 to a bone. Cut-out 42 in outwardly facing surface 24 provides clearance for the patella when provisional component 20 is mounted on a femur 23.

A second provisional component 44 is shown in FIG. 8. First and second provisional components 20, 44 are both stainless steel components. Provisional component 44 is removably mountable on the proximal end of a tibia 46. Second provisional component 44 has a mounting surface 48 which engages a resected surface 52 of tibia 46 and an opposite bearing surface 50 which is engageable with outwardly facing surface 24 as discussed in greater detail below. Alternatively, the tibial provisional component may take the form of a solid plate having a thickness and shape similar to that of second provisional component 44 and a rod shaped handle projecting from an edge of the plate that may be used to hold the component in place.

Figure 6:
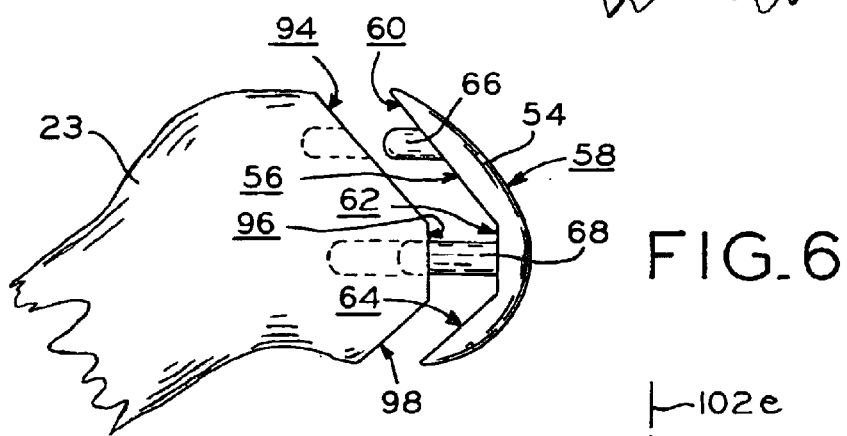
FIG. 6 is a view of a femur and a femoral component of a permanent orthopedic prosthesis.

The provisional orthopedic prosthesis formed by provisional components 20 and is used to assess the fit of a permanent orthopedic prosthesis prior to implanting the femoral component 54 and tibial component 70 which form the permanent prosthesis. As best seen in FIG. 6, permanent femoral component 54 includes a bone engaging surface 56 and an oppositely disposed articulating surface 58. The illustrated embodiment is a unicompartmental prosthesis wherein articulating surface 58 defines a single condylar-shaped projection. Similarly, the outwardly facing articulating surface 24 of provisional component 20 defines a single condylar-shaped projection. The present invention, however, could also be utilized with total knee joints in which the femoral component includes two condylar-shaped projections and at other anatomical locations. In the illustrated embodiment, bone engaging surface 56 is formed by three intersecting planar surfaces 60, 62, 64 which engage bone surfaces 94, 96, 98 formed by a distal cut, a chamfer cut and a posterior cut respectively. Two mounting posts 66, 68 are also located on the inward facing surface 56 of permanent component 54 and are inserted into cylindrical bores drilled into femur 23 when implanting femoral component 54 on femur 23.

Figure 7:
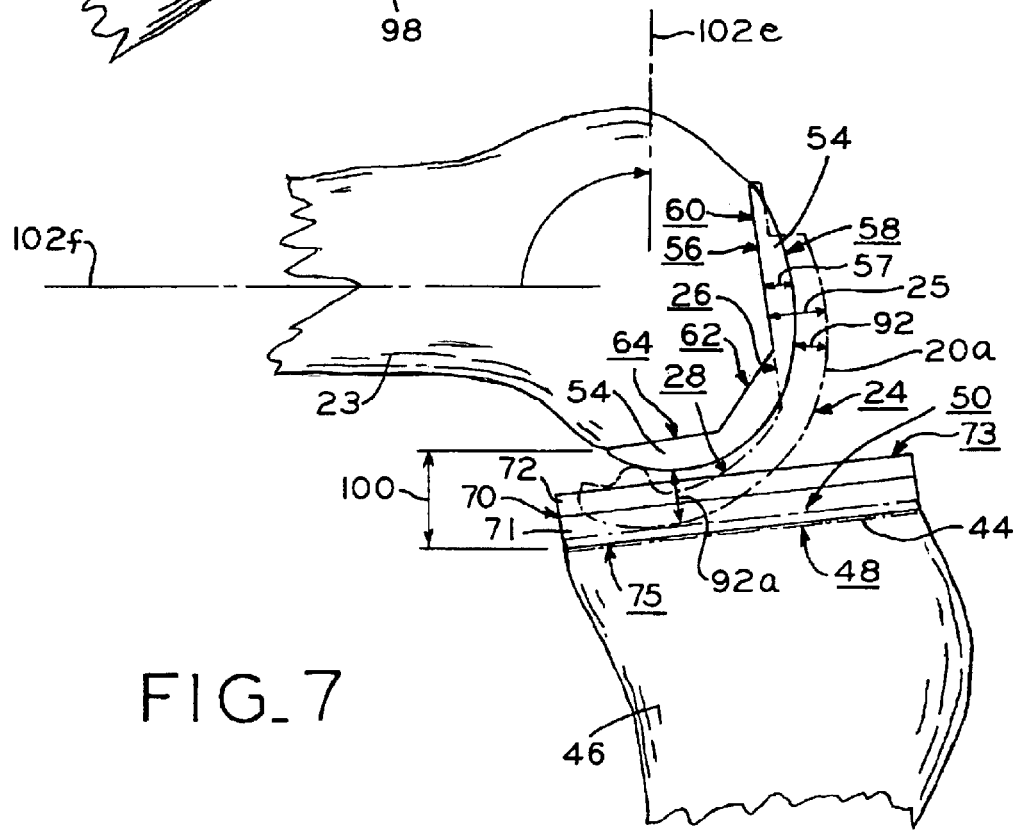
FIG. 7 is a view of a femur and a tibia, a permanent orthopedic prosthesis and the outline of a provisional prosthesis.

Tibial component 70 is shown in FIG. 7 and includes a stainless steel base plate 71 and polyethylene bearing member 72. The upper surface 73 of member 72 forms a bearing surface engageable with femoral component 54 and the lower surface 75 of base plate 71 engages and is mounted on resected surface 52 of tibia 46. The orthopedic prosthesis formed by stainless steel permanent femoral component 54 and permanent tibial component 70 and instrument guide 74 are known in the art and commercially available from Zimmer Inc. of Warsaw, Ind. under the name M/G™ Unicompartmental Knee.

Instrument guide 74 is shown in FIGS. 9 and 10. Instrument guide 74 includes two cut slots 76, 78 and two drill guides 82, 84. Instrument guide 74 also includes two mounting holes 86 which receive headless mounting pins 90 when mounting instrument guide 74 to femur 23. The use of instrument guide 74 is discussed in greater detail below.

The use of provisional component 20 in a surgical procedure to implant a permanent orthopedic prosthesis will now be discussed. FIG. 5 illustrates a right femur 23 and tibia 46 in flexion. In FIG. 5, the right lateral tibial plateau has been resected leaving surface 52 and the distal portion of the right lateral condyle has been resected leaving surface 94. Provisional component 20 is mounted on distal femur 23 by engaging a T-shaped handle with threaded opening 30 and positioning component 20 such that planar surface 26 engages resected surface 94. After component 20 has been properly positioned in the anterior/posterior direction, a securement member, such as a bone screw having a threaded shaft and a head (not shown) is positioned within oval opening 40 and secured to femur 23. The use of oval opening 40 allows provisional component 20 to be adjusted in the lateral/medial direction and rotated about the bone screw before tightening the bone screw to secure provisional component 20 in place. After securing provisional component 20 to femur 23, the T-shaped handle is disengaged from provisional component 20.

Provisional component 20 is secured to femur 23 in the position shown in dashed outline in FIG. 7. FIG. 7 also illustrates permanent femoral component 54 in its implanted position on femur 23. As can be seen with reference to FIG. 7, the first planar portion 26 of inwardly facing surface 22 has a configuration that substantially conforms to planar surface 60 which forms a part of the bone engaging surface 56 of femoral component 54. Thus, first surface portion 26 is adapted to be mounted on a bone surface, such as surface 94, which has been resected to receive planar surface 60. The resection of a femur to form a resection surface such as surface 94 is well known in the art. The resection of a tibial plateau to form resection surface 52 is also well known in the art.

Outer surface 58 of implanted femoral component 54 generally takes the form of the original external surface of femur 23. As best seen in FIG. 7, the posterior portion of provisional component 20 which includes second portion 28 of inwardly facing surface 22 is positioned sufficiently outwardly to enable provisional component 20 to be mounted to resected surface 94 prior to resecting any additional portion of femur 23 posterior to resected surface 94, i.e., prior to forming chamfer cut 96 or posterior cut 98. Thus, provisional component 20 does not have a configuration which is identical to permanent femoral component 54. As can also be seen in FIG. 7, the second portion 28 of inward facing surface 22 of provisional component 20 is positioned outwardly relative to the corresponding bone engaging surfaces 62, 64 of femoral component 54. Consequently, inward facing surface 22 defines a greater volume than the volume defined by bone engaging surface 56 and thereby enables provisional component 20 to be mounted on femur 23 prior to forming chamfer cut 96 and posterior cut 98. Despite its larger outer surface, provisional femoral component 20, however, can still be used to assess the fit of permanent femoral component 54.

As shown in FIG. 7, a permanent component spacing 57 between surfaces 60 and 58 of component 54 proximate resection surface 94 is less than provisional component spacing 25 between inward facing planar surface 26 and outer surface 24 at the corresponding location on provisional component 20. The difference between provisional component spacing 25 and permanent component spacing 57 is represented as dimension 92. (Although FIG. 7 illustrates dimension lines 25, 57 and 92 at slightly offset positions to enhance the clarity of the figure, these dimension lines all represent the described distances at the location of line 25.) Because surface 26 has the same configuration as bone engaging planar surface 60 at the location of spacings 25, 57, the difference 92 represents the distance by which outer provisional surface 24 projects beyond the outer surface 58 of femoral component 54. In the illustrated embodiment, dimension 92 is approximately 6 to 8 mm. Along the posterior section of provisional component 20 the thickness of the provisional component 20 between outwardly facing surface 24 and inwardly facing surface 22 has been reduced to adapt the posterior section of provisional component 20 for placement adjacent a non-resected surface of femur 23. The distance by which outwardly facing surface 24 projects beyond outer surface 58 of femoral component 54 along this posterior section of provisional component 20 is represented by dimension line 92a. Although FIG. 7 is not drawn precisely to scale, the distance by which outwardly facing surface 24 projects beyond outer surface 58 is a substantially constant value and dimensions 92 and 92a are substantially equivalent to enable provisional component 20 to be used to assess the fit of femoral component 54.

By maintaining outer provisional surface 24 at a substantially constant projection distance relative to the location of outer surface 58 of femoral component 54, the thickness of tibial provisional component 44, represented in dashed outline in FIG. 7, can be reduced relative to permanent tibial component 70 by the same distance 92. This allows provisional component 20 to be used in conjunction with relatively thin provisional component 44 to assess the fit of the prosthesis formed by femoral component 54 and tibial component 70 after making only one of the three resections necessary to implant femoral component 54.

After mounting provisional components 20, 44 on femur 23 and tibia 46, a trial reduction is performed. In other words, femur 23 and tibia 46 are re-engaged and moved through a range of motion from a flexion position to an extension position to assess the fit of provision component 20. FIG. 7 illustrates femur 23 and tibia 46 in flexion. In FIG. 7, axis 102f indicates the position of the anatomical axis of femur 23 relative to tibia 46 in flexion and axis 102e indicates the position of the anatomical axis of femur 23 when femur 23 and tibia 46 are placed extension. The anatomical axis femur 23 is defined by the femoral medullary canal. Throughout this range of motion, by having outer surface 24 of provisional component 20 project a constant distance 92 outwardly toward tibia 46 and configuring tibial provisional component 44 to have a thickness which is less than tibial component 70 by distance 92, the provisional prosthesis formed by components 20, 44 can be used to assess whether the preliminarily selected permanent components 54, 70 are the proper selection. During this assessment, the surgeon will examine the tightness of the ligaments and other soft tissues and other attributes of the joint in the same manner that would be employed if conventional provisional components having the same shape and size as the permanent components had been mounted to femur 23. It is also possible to avoid the use of a tibial provisional component by configuring femoral provisional component 20 so that projection distance 92 is substantially equivalent to the thickness of the permanent tibial component 70. In such an alternative embodiment, provisional component 20 would bear directly on resection surface 52 during the assessment of the fit of provisional component 20.

Outer surface 58 of femoral component 54 defines a condyle-shaped projection forming an articulating surface that bears against an opposed bearing surface 73 on tibial component 70. In actual use, the motion of femoral component 54 relative to tibial component 70 is primarily rotational but also includes a relatively small anterior/posterior sliding component. Because of the complex nature of outer surface 58 and of the relative rotational and sliding motion of femoral component 54, provisional component 20 with its larger articulating surface 24 provides only an approximation of the fit that will be realized by the implantation of femoral component 54 and tibial component 70. This approximation, however, is considered sufficiently accurate to provide a meaningful assessment of the likely fit of femoral component 54 and tibial component 70.

Since only one, i.e., distal femoral cut 94, of the three planar cuts 94, 96, 98 is completed before mounting provisional component 20 on femur 23, provisional component 20 can only be used to directly assess the gap between distal femoral cut 94 and proximate tibial cut 52. The gap between the resected surfaces on femur 23 and resected surface 52 is designated by dimension line 100. In FIG. 7, femur 23 must be rotated to the extension position represented by axis 102e for femur 23 and tibia 46 to be properly positioned to assess gap 100 formed between surfaces 94 and 52. Similarly, FIG. 5 illustrates femur 23 and tibia 46 in a flexion position and relative rotation of tibia 46 and femur 23 to an extension position will position surface 94 at a distance 100 from surface 52.

The provisional mounting distance defined by the combination of provisional component spacing 25 and the thickness of the tibial component 44 is, when provisional components 20, 44 fit properly, substantially equivalent to gap distance 100 defined by surfaces 94 and 52 with femur 23 and tibia 46 in extension. Similarly, the mounting distance defined by the combination of permanent component spacing 57 and the thickness of tibial component 70, when permanent components 54, 70 fit properly, is also substantially equivalent to gap distance 100 defined by surfaces 94 and 52 with femur 23 and tibia 46 in extension. The use of planar cuts to form an arcuate cross section on femur 23 results in a non-homogenous thickness for the components mounted thereon. The value of such mounting distances to assess prepared surfaces on the bones (e.g., resected surfaces 94 and 52) is meaningful if the compared distances defined by the provisional and permanent components utilize the same orientation and location relative to the bones receiving the prostheses and are at a location wherein the mounting distance defined by the provisional prosthetic components separate bone surfaces which have already been prepared to receive the permanent prosthetic components. For example, such a mounting distance of the provisional and permanent components includes the distance defined by these prosthetic components when bone surfaces 94 and 52 are mutually parallel along a line which is perpendicular to surfaces 94, 52 and intersects the location where the first and second prosthetic components are engaged.

Alternatively, if no provisional tibial component 44 is used and provisional component 20 bears directly against surface 52 to assess the fit of provisional component 20, the thickness of provisional component 20 represented by spacing distance 25 will be substantially equivalent to gap 100 defined by surfaces 94 and 52. Alternative embodiments of provisional component 44 may also include a secondary member placed between base provisional member 44 and femoral provisional component 20. In such an alternative embodiment, the thickness of the secondary member together with the thickness of base provisional component 44 would need to be considered instead of the thickness of provisional component 44 alone when assessing the various distances discussed above.

After securing provisional component 20 in place using a bone screw positioned within opening 40, alignment members such as headless mounting pins 90 are installed in femur 23 by inserting pins 90 through guide elements 34. Guide elements 34 are positioned on provisional component 20 so that pins 90 inserted therethrough will be mounted on femur 23 in positions which will properly locate instrument guide 74 on femur 23 to prepare femur 23 to receive femoral component 54. Instead of installing pins 90 before assessing the fit of provisional component 20, pins 90 may alternatively be installed after assessing the fit of provisional components 20, 44. In this alternative approach, if provisional component 20 does not fit properly, pins 90 will not have been needlessly inserted into femur 23.

If the assessment of illustrated provisional component 20 indicates that it does not fit properly, a differently sized provisional femoral component which is configured to assess the fit of a differently sized permanent femoral component is mounted on femur 23. An advantage of provisional component 20 is that, if the preliminarily selected femoral component 54 is not the correct size, only one resection, i.e., resection 94, has been made on femur 23 instead of three resections, i.e., 94, 96, 98, and preparing femur 23 to accept the differently sized femoral component is greatly simplified. For example, the change in component sizes may only require that instrument guide 74 be positioned differently on resection surface 94 or that a different instrument guide be positioned on resection surface 94 to prepare femur 23 to receive the alternatively sized femoral component. Such a change may also require that resection surface 94 (i.e., the distal cut) be recut prior to making the chamfer and posterior cuts, however, in such a situation only one surface would have to be recut.

If the assessment of provisional component 20 indicates that preliminarily selected femoral component 54 is the appropriately sized prosthetic component, provisional component 20 removed from femur 23 by removing the bone screw attached through opening 40 and sliding provisional component 20 off pins 90. Pins 90 are left secured to femur 23. Instrument guide 74 is then attached to femur 23 by sliding the projecting ends of pins 90 into mounting holes 86. FIG. 9 shows a pin 90 separate from femur 23. Illustrated pin 90 includes a removable collar 91 that may be attached to pin 90 after mounting instrument guide 74 on pins 90 to facilitate the securement of instrument guide 74 on femur 23. Holding pin 90 and collar 91 are known in the art.

After mounting instrument guide 74 on pins 90, electrocautery may be used to mark the bone anterior/superior to distal cut 94 above the center of instrument guide 74. This mark provides a reference point that can be used to help ensure that instrument guide 74 remains in the desired position. Bone screws or holding pins are then attached to femur 23 through openings 87, 88 to secure instrument guide 74. Pins 90 located in openings 86 may be removed after securing instrument guide 74 with fasteners in openings 87, 88. Pins 90 may be left in openings 86 if femur 23 does not have adequate bone material to secure instrument guide using openings 87, 88. A bone screw or holding pin may also be attached through opening 89 to secure instrument guide 74 if necessary.

Once instrument guide 74 has been securely mounted to femur 23, a drill bit is sequentially inserted through drill guides 82, 84 and bores 83, 85 (shown in dashed outline) are formed in femur 23 to receive posts 68, 66 of femoral component 54. Drill guides 82, 84 are formed by cylindrical openings through instrument guide 74.

A cutting blade or other suitable instrument is then inserted into cut slot 76 to perform the chamfer cut (surface 96) until the cutting blade almost contacts the bone screws or holding pins securing instrument guide 74 in place. The cutting blade is then inserted in cutting slot 78 to perform the posterior cut (surface 98). After removal of the instrument guide 74, the chamfer cut 96 and posterior cut 98 are completed and any prominences or uncut bone remaining on surfaces 96, 98 are removed. The resections and bores formed using instrument guide 74 may also be formed in alternative orders.

An alternative method of providing an instrument guide to resect femur 23 that may be used with the present invention is described in U.S. Patent Application Publication No. US 2004/0153087 A1. application Ser. No. 10/358.010. entitled PROVISIONAL ORTHOPEDIC IMPLANT HAVING REMOVABLE GUIDE. filed on Feb. 4, 2003, the disclosure of which is hereby expressly incorporated herein by reference. In this alternative approach, a modular guide element is secured directly to the provisional component and the provisional component forms a part of the instrument guide used in the preparation of the femur.

After femur 23 has been prepared to receive permanent implant 54, a final provisional component having a configuration and size which is identical to permanent component 54 is mounted on femur 23 by inserting mounting posts on the provisional component into bores 83, 85 on femur 23. A provisional tibial component having the same thickness as permanent component 70 is placed on surface 52 and the fit of components 54, 70 is assessed again prior to implanting components 54, 70. A final provisional component which provides for the mounting of a guide instrument to femur 23 for recutting femur 23 in the event that the provisional component indicates that a different sized femoral component is required is described in U.S. Patent Application Publication No. US 2004/0153086 A1. application Ser. No. 10/357,721, entitled PROVISIONAL ORTHOPEDIC IMPLANT AND RECUTTING INSTRUMENT GUIDE, filed on Feb. 4, 2003, the disclosure of which is hereby expressly incorporated herein by reference.

If the trial reduction using the final provisional components is successful, the final provisional components are removed and tibial component 70 and femoral component 54 are implanted on tibia 46 and femur 23 respectively. Tibial component 70 and femoral component 54 are implanted in a conventional manner employing bone cement.

While this invention has been described as having an exemplary design, the present invention may be further modified within the spirit and scope of this disclosure. This application is therefore intended to cover any variations, uses, or adaptations of the invention using its general principles.

What is claimed is:

1. A provisional orthopedic prosthesis for facilitating the selection of a permanent orthopedic prosthesis having a permanent component with a bone engaging surface, an oppositely disposed articulating surface and defining a permanent component spacing therebetween, said provisional prosthesis comprising:
a first provisional component having an inwardly facing surface and an outwardly facing surface; said inwardly facing surface having a first portion defining a configuration substantially similar to a portion of the bone engaging surface of the permanent component and a second portion adapted for placement facing a non-resected bone surface; said outwardly facing surface defining a first articulating surface at least partially disposed opposite each of said first and second portions of said inwardly facing surface and defining a provisional spacing between said outwardly facing surface and said first portion greater than said permanent component spacing.

2. The provisional orthopedic prosthesis of claim 1 wherein said first provisional component further defines at least one guide element having a predefined position relative to said first portion.

3. The provisional orthopedic prosthesis of claim 2 wherein said at least one guide element comprises an opening extending from said outwardly facing surface to said first portion of said inwardly facing surface.

4. The provisional orthopedic prosthesis of claim 1 wherein provisional spacing is approximately six to eight millimeters greater than the permanent component spacing.

5. The provisional orthopedic prosthesis of claim 1 further comprising a second provisional component mountable on a second bone and having a second bearing surface engageable with said first articulating surface and a mounting surface engagable with a resected bone surface, said first and second provisional components defining a provisional mounting distance between said first portion of said inwardly facing surface and said mounting surface; said provisional mounting distance being substantially equivalent to a corresponding mounting distance occupied by the permanent orthopedic prosthesis.

6. The provisional orthopedic prosthesis of claim 5 wherein said first provisional component is adapted for placement on a distal femur and said articulating surface of said first provisional component defines a single condylar-shaped projection and said second provisional component is adapted for placement on a proximal tibia.

7. A provisional orthopedic prosthesis for facilitating the selection of a permanent orthopedic prosthesis having a permanent component with a bone engaging surface defining a plurality of intersecting planar surfaces, an oppositely disposed articulating surface and defining a permanent component spacing therebetween, said provisional prosthesis comprising:
a first provisional component having an inwardly facing surface and an outwardly facing surface; said inwardly facing surface having a first portion defining a substantially planar surface lying within a single plane and configured substantially similar to a portion of the bone engaging surface of the corresponding permanent prosthesis and a second portion positionable proximate a non-resected bone surface; said outwardly facing surface defining a first articulating surface at least partially disposed opposite each of said first and second portions of said inwardly facing surface and defining a provisional spacing between said outwardly facing surface and said first portion greater than the permanent component spacing.

8. The provisional orthopedic prosthesis of claim 7 wherein said first provisional component further defines at least one guide element having a predefined position relative to said first portion.

9. The provisional orthopedic prosthesis of claim 8 wherein said at least one guide element comprises an opening extending from said outwardly facing surface to said first portion of said inwardly facing surface.

10. The provisional orthopedic prosthesis of claim 7 wherein provisional spacing is approximately six to eight millimeters greater than the permanent component spacing.

11. The provisional orthopedic prosthesis of claim 7 further comprising a second provisional component mountable on a second bone and having a second bearing surface engageable with said first articulating surface and a mounting surface engagable with a resected bone surface, said first and second provisional components defining a provisional mounting distance between said first portion of said inwardly facing surface and said mounting surface; said provisional mounting distance being substantially equivalent to a corresponding distance occupied by the permanent orthopedic prosthesis.

12. The provisional orthopedic prosthesis of claim 11 wherein said first provisional component is adapted for placement on a distal femur and said articulating surface of said first provisional component defines a single condylar-shaped projection and said second provisional component is adapted for placement on a proximal tibia.

13. An orthopedic prosthesis system comprising:
a permanent prosthesis including a first permanent component defining a bone engaging surface and an oppositely disposed articulating surface, said bone engaging surface and said articulating surface defining a permanent component spacing therebetween; and
a first provisional component having an inwardly facing surface and an outwardly facing surface, said inwardly facing surface having a first portion defining a configuration substantially similar to a portion of said bone engaging surface and a second portion adapted for placement facing a non-resected bone surface, said outwardly facing surface defining a first articulating surface at least partially disposed opposite each of said first and second portions of said inwardly facing surface and defining a provisional component spacing between said outwardly facing surface and said first portion, said provisional component spacing being greater than said permanent component spacing, said provisional component defining a second thickness between said second portion of said inwardly facing surface and said outwardly facing surface wherein a substantial portion of said second thickness is less than the difference between said provisional component spacing and said permanent component spacing.

14. The system of claim 13 further comprising an alignment member removably securable to the bone wherein said first provisional component includes at least one guide element for positioning said alignment member relative to the bone and wherein said system further includes an instrument guide alignable with said alignment member.

15. The system of claim 13 wherein said permanent orthopedic prosthesis further comprises a second permanent component having a second bone engaging surface and a permanent bearing surface engageable with said articulating surface of said first permanent component, said second bone engaging surface and said bone engaging surface of said first permanent component defining a prosthetic mounting distance therebetween;

said system further comprising a second provisional component having a mounting surface engageable with a bone and a second bearing surface engageable with the first articulating surface, said first and second provisional components defining a provisional mounting distance between said first portion of said first provisional component and said mounting surface that is substantially equivalent to said prosthetic mounting distance.

16. The system of claim 13 wherein said at least one permanent orthopedic prosthesis is a prosthetic knee joint and said articulating surface of said first permanent component defines a single condylar-shaped projection.

17. The system of claim 13 wherein said provisional component spacing is approximately six to eight millimeters greater than said permanent component spacing.

18. The system of claim 13 wherein said bone engaging surface of said permanent component defines a plurality of intersecting planar surfaces and wherein said first portion of said inwardly facing surface of said provisional component is substantially planar.

19. A method of implanting an orthopedic prosthesis at a joint between a first bone and a second bone, said method comprising:

providing a provisional prosthesis and a corresponding permanent prosthesis, said permanent prosthesis having first and second permanent components, said first permanent component having a bone engaging surface and an oppositely disposed articulating surface defining a permanent component spacing therebetween, said provisional prosthesis having a first provisional component having an inwardly facing surface and an outwardly facing surface, said inwardly facing surface having a first portion defining a configuration substantially similar to a portion of said bone engaging surface and a second portion adapted for placement facing a non-resected bone surface;

partially preparing the first bone to receive the permanent component;

mounting the first provisional component on the first bone wherein said outwardly facing surface of said first provisional component opposite said first portion of said inwardly facing surface is spaced outwardly from the bone by a distance which is greater than said permanent component spacing;

assessing the fit of said provisional prosthesis; and completing the preparation of the first bone after assessing the fit of said provisional prosthesis.

20. The method of claim 19 wherein said step of partially preparing the first bone includes resecting a portion of the first bone to form a substantially planar resection surface on the first bone; wherein said step of mounting said first provisional component to the first bone includes engaging a first portion of said inwardly facing surface with the resection surface and positioning a second portion of said inwardly facing surface adjacent a non-resected surface of the first bone; and wherein said step of completing the preparation of the first bone includes resecting a portion of the first bone defined by the non-resected surface of the first bone.

21. The method of claim 20 wherein the first bone is a femur and said articulating surface of said first permanent component has a single condylar-shaped projection.

22. The method of claim 19 further comprising the step of at least partially preparing the second bone to receive said permanent prosthesis and wherein said steps of partially preparing the first and second bones defines a gap between first and second prepared surfaces located respectively on the first and second bones and wherein said step of assessing the fit of said provisional prosthesis includes assessing the fit of said provisional prosthesis within the gap.

23. The method of claim 22 wherein said provisional prosthesis includes a second provisional component mountable on the second bone and having a second bearing surface engageable with said outwardly facing surface of said first provisional component and a mounting surface engageable with the second bone, said first and second provisional components defining a provisional mounting distance between said first portion of said inwardly facing surface of said first provisional component and said mounting surface of said second provisional component, said provisional mounting distance being substantially equivalent to a corresponding mounting distance occupied by the permanent prosthesis and wherein assessing the fit of said provisional prosthesis within the gap includes positioning said first and second provisional components to separate the first and second bones by said provisional mounting distance.

* * * * *